United States Patent [19] [11] 3,971,792
Zondler et al. [45] July 27, 1976

[54] PROCESS FOR THE MANUFACTURE OF 4-AMINO-3-AMINOMETHYLPIPERIDINE

[75] Inventors: Helmut Zondler, Allschwil, Switzerland; Wolfgang Pfleiderer, Constance, Germany

[73] Assignee: Ciba-Geigy AG, Basel, Switzerland

[22] Filed: June 10, 1974

[21] Appl. No.: 477,890

Related U.S. Application Data

[60] Continuation-in-part of Ser. No. 316,308, Dec. 18, 1972, abandoned, which is a division of Ser. No. 125,382, March 17, 1971, Pat. No. 3,717,593.

[30] Foreign Application Priority Data
Mar. 23, 1970 Switzerland.......................... 4337/70

[52] U.S. Cl. ........................................... 260/293.52
[51] Int. Cl.$^2$...................................... C07D 211/98
[58] Field of Search ............................... 260/293.52

[56] References Cited
UNITED STATES PATENTS
3,481,938 12/1969 Chicherry et al.............. 260/293.52
3,658,824 4/1972 Thoma et al................... 260/293.52
3,717,593 2/1973 Zondler et al...................... 260/2 N Primary Examiner—G. Thomas Todd
Attorney, Agent, or Firm—Vincent J. Cavalieri

[57] ABSTRACT

The new compound 4-amino-3-aminomethylpiperidine is manufactured by hydrogenating 4-amino-3-cyano-1,2,5,6-tetrahydropyridine under pressure and in the presence of ammonia and a hydrogenation catalyst. The 4-amino-3-cyano-1,2,5,6-tetrahydropyridine used as the starting substance can be obtained by cyclization of bis-cyanoethylenated ammonia. The new compound 4-amino-3-aminomethylpiperidine represents a valuable curing agent for epoxide resins, and advantageously 0.5 to 1.3 equivalents of nitrogen-bonded active hydrogen atoms of the 4-amino-3-aminomethylpiperidine are used per 1 equivalent of epoxide groups of the polyepoxide compound.

8 Claims, No Drawings

PROCESS FOR THE MANUFACTURE OF 4-AMINO-3-AMINOMETHYLPIPERIDINE

This application is a continuation-in-part of application Ser. No. 316,308 filed Dec. 18, 1972, now abandoned, which application is in turn a divisional application of application Ser. No. 125,382, filed Mar. 17, 1971, now U.S. Pat. No. 3,717,593.

The present invention provides a process for the manufacture of 4-amino-3-aminomethylpiperidine of the formula

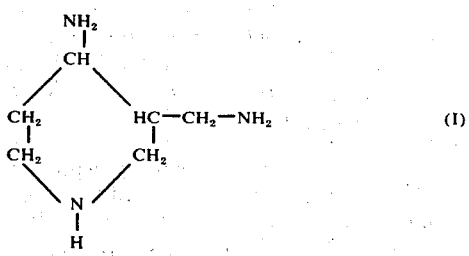

which is characterised in that 4-amino-3-cyano-1,2,5,6-tetrahydropyridine of the formula

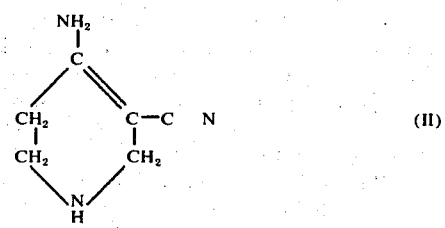

is hydrogenated under pressure and in the presence of ammonia and a hydrogenation catalyst.

Raney nickel or Raney cobalt are particularly effective as hydrogenation catalysts. It is also possible to use a cobalt oxide catalyst on a suitable carrier material, this catalyst being reduced to cobalt metal catalyst in the stream of hydrogen.

Further possible hydrogenation catalysts are catalysts based on platinum and palladium which can be employed as platinum black or palladium black, as colloidal platinum or palladium, or as platinum oxide or palladium oxide, or platinum hydroxide or palladium hydroxide, catalysts. Possible carrier materials for such catalysts are the customary materials, such as asbestos, pumice, kieselgur, silica gel, silica, active charcoal, and the sulphates, carbonates or oxides of the metals of Groups II to VIII of the periodic system, especially of magnesium, calcium, barium, zinc, aluminium, iron, chromium and zirconium.

A preferred manner of the invention is a hydrogenation in the presence of an organic solvent. Solvents which can be used in the hydrogenation are the organic solvents which are customarily employed together with the abovementioned types of catalyst, and in particular, preferably, lower aliphatic alcohols, such as methanol or ethanol.

The catalytic reduction is as a rule carried out by mixing the suspension or solution of the 4-amino-3-cyano-1,2,5,6-tetrahydropyridine with the ammonia and hydrogenation the catalyst and passing hydrogen gas into the reaction mixture. The hydrogenation can in principle be carried out at room temperature and preferably at pressures or 50 atmospheres and above. Elevated reaction temperatures in the range of 50° to 150°C are preferred. The hydrogenation is continued until no further hydrogen is absorbed. After completion of the hydrogenation the catalyst is separated off, for example by filtration, and the solvent is distilled off.

The process according to the invention leads, surprisingly to a pure product with high yields being obtained. If no ammonia is present during hydrogenation, the yield is very small.

The 4-amino-3-cyano-1,2,5,6-tetrahydropyridine used as a starting substance can be obtained by cyclisation of bis-cyanoethylated ammonia of the formula

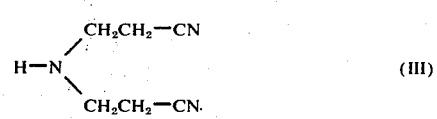

The new compound 4-amino-3-aminomethyl-piperidine represents a valuable curing agent for epoxide resins.

Curable mixtures which are suitable for the manufacature of shaped articles, impregnations, coatings and adhesive bonds contain (a) a polyepoxide compound with an average of more than one epoxide group in the molecule and (b) 4-amino-3-aminomethyl-piperidine as the curing agent.

Appropriately, 0.5 to 1.3 equivalents, preferably approx. 1.0 equivalent, of nitrogen-bonded active hydrogen atoms of the 4-amino-3-aminomethyl-piperidine are used per 1 equivalent of epoxide groups of the polyepoxide compound (a).

Possible polyepoxide compounds (a) are above all those with an average of more than one glycidyl group, $\beta$-methylglycidyl group or 2,3-epoxycyclopentyl group bonded to a hetero-atom (for example sulphur, preferably oxygen or nitrogen); in particular, there may be mentioned bis-(2,3-epoxycyclopentyl) ether; diglycidyl ethers and polyglycidyl ethers of polyhydric aliphatic alcohols, such as 1,4-butanediol, or polyalkylene glycols, such as polypropylene glycols; diglycidyl ethers or polyglycidyl ethers of cycloaliphatic polyols, such as 2,2-bis-(4-hydroxycyclohexyl) propane; diglycidyl ethers and polyglycidyl ethers of polyhydric phenols, such as resorcinol, bis-(p-hydroxyphenyl) methane, 2,2-bis (p-hydroxyphenyl)-propane (=Diomethan), 2,2-bis(4'-hydroxy-3',5' -dibromophenyl)-propane, 1,1,2,2,-tetrakis-(p-hydroxyphenyl)-ethane or of condensation products of phenols with formaldehyde, obtained under acid conditions, such as phenol novolacs and cresol novolacs; di- and poly-($\beta$-methylglycidyl) ethers of the abovementioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; n-glycidyl derivatives of amines, amides and heterocyclic nitrogen bases, such as N,N-diglycidyl-aniline, N,N-diglycidyl-toluidine, and N,N,N',N'-tetraglycidyl-bis-(p-aminophenyl)-methane; triglycidylisocyanurate, N,N'-diglycidyl-5,5-dimethylhydantoin, N,N'-diglycidyl-5-isopropyl-hydantoin; N,N'diglycidyl-5,5-dimethyl-6-isopropyl-5,6-dihydrouracil.

If desired, active diluents, such as for example, styrene oxide, butyl glycidyl ether, isooctyl glycidyl ether, phenyl glycidyl ether, cresyl glycidyl ether or glycidyl esters of synthetic, highly branched, mainly tertiary aliphatic monocarboxylic acids ("CARDURA E") can be added to the polyepoxides to reduce the viscosity.

The curing of the curable mixtures to give shaped articles and the like is appropriately carried out in the temperature range of 20° to 150°C. The curing can also be carried out in a known manner in two or more stages, with the first curing stage, for example, being carried out at room temperature and the post-curing being carried out at a higher temperature.

The curing can, if desired, also be carried out in two stages by first prematurely stopping the curing reaction or carrying out the first stage at room temperature or only slightly elevated temperature, whereby a curable precondensate (so-called "B-stage") which is still fusible and soluble is obtained from the epoxide component (a) and the amine curing agent (b). Such a precondensate can for example serve for the manufacture of "prepegs", compression moulding compositions or especially sintering powders.

In order to shorten the gelling times or curing times, known accelerators for curing with amines, for example monophenols or polyphenols, such as phenol or diomethane, salicylic acid, tertiary amines or salts of thiocyanic acids, such as NH$_4$SCN, can be added.

The term "cure" as used here denotes the conversion of the soluble, either liquid or fusible, polyepoxides into solid, insoluble and infusible, three-dimensionally cross-linked products or materials, and in particular, as a rule, with simultaneous shaping to give shaped articles, such as castings, pressings, laminates and the like, or "sheet-like structures," such as coatings, lacquer films or adhesive bonds.

The curable mixtures can further be mixed, in any stage before curing, with customary modifiers, such as extenders, fillers and reinforcing agents, pigments, dyestuffs, organic solvents, plasticisers, flow control agents, flameproofing substances or mould release agents.

As extenders, reinforcing agents, fillers and pigments which can be employed in the curable mixtures there may, for example, be mentioned: coal tar, bitumen, textile fibres, glass fibres, asbestos fibres, boron fibres, carbon fibres, cellulose, polyethylene powder, polypropylene powder, polypropylene powder; quartz powder, mineral silicates, such as mica, asbestos powder and slate powder; kaolin, aluminium oxide trihydrate, chalk powder, gypsum, antimony trioxide, bentones, silica aerogel ("AEROSIL"), lithopone, baryte, titanium dioxide, carbon black, graphite, oxide colours, such as iron oxide, or metal powders, such as aluminium powder or iron powder.

Suitable organic solvents for modifying the curable mixtures are, for example, toluene, xylene, n-propanol, butyl acetate, acetone, methyl ethyl ketone, diacetone-alcohol, ethylene glycol monomethyl ether, monoethyl ether and monobutyl ether.

Dibutyl phthalate, dioctyl phthalate and dinonyl phthalate, tricresyl phosphate, trixylenyl phosphate and also polypropylene glycols can for example be employed as plasticisers for modifying the curable mixtures.

Silicones, cellulose acetobutyrate, polyvinyl butyral, waxes, stearates and the like (which are in part also used as mould release agents) can for example be employed as flow control agents when using the curable mixtures, especially in surface protection.

For use in the lacquer field, in particular, the polyepoxide compounds can further be partially esterified in a known manner with carboxylic acids, such as, especially, higher unsaturated fatty acids. It is furthermore possible to add other curable synthetic resins, for example phenoplasts or aminoplasts, to such lacquer resin formulations.

The curable mixtures can be manufactured in the customary manner with the aid of known mixing equipment (stirrers, kneaders, rolls and the like).

The curable epoxide resin mixtures are above all employed in the fields of surface protection, the electrical industry, laminating processes and the building industry. They can be used, in each case in a formulation adapted to the particular end use, in the unfilled or filled state, and optionally in the form of solutions or emulsions, as paints, lacquers, sintering powders, compression moulding compositions, injection moulding formulations, dipping agents, casting resins, impregnating resins, binders and adhesives, tool resins, laminating resins, sealing and filling compositions, floor covering compositions and binders for mineral aggregates.

In the examples which follow, unless otherwise indicated, parts denote parts by weight and percentages denote percentages by weight. The relationship of parts by volume to parts by weight is as of the milliliter to the gram.

The following epoxide resins were used for the manufacture of curable mixtures described in the examples.

Epoxide Resin A

Diglycidal ether resin (technical product) manufactured by condensation of diomethane (2,2-bis(p-hydroxyphenyl)-propane) with a stoichiometric excess of epichlorohydrin in the presence of alkali, consisting mainly of diomethanediglycidyl ether of the formula

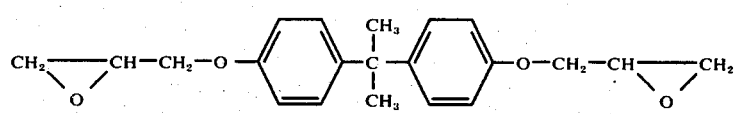

which is liquid at room temperature and has the following characteristics:
Epoxide content: 5.1 - 5.5 epoxide equivalents/kg
Viscosity (Hoeppler) at 25°C: 9000 –13,000cP.

Epoxide Resin B

Diglycidyl ether resin (technical product) manufactured by condensation of hydrogenated diomethane (2,2-bis-(p-hydroxycyclohexyl)-propane) with a stoichiometric excess of epichlorohydrin in the presence of alkali, consisting mainly of hydrogenated diomethanediglycidal ether of the formula

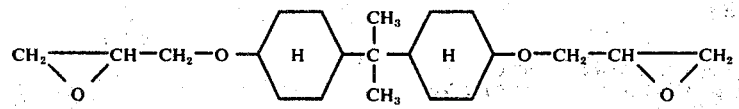

which is liquid at room temperature and has an epoxide content of 4.46 epoxide equivalents/kg.

Epoxide Resin C

Tetrahydrophthalic acid diglycidyl ester having the following characteristics:
Epoxide content: 6.45 equivalents/kg
Viscosity (Hoeppler) at 25°C: 450–550 cP.

To determine the mechanical and electrical properties of the mouldings which can be manufactured from the curable mixtures described in the examples which follow, sheets of size 135 × 135 × 4 mm were manufactured for determining the flexural strength, deflection, impact strength and water absorption. The test specimens (60 ×0 10 × 4 mm) for determining the water absorption and for the flexural test and impact test (VSM 77,103 and VSM 77,105) were machined from the sheets.

Manufacturing Example

4-Amino-3-aminomethyl-piperidine a. 160 g of 4-amino-3-cyano-1,2,5,6-tetrahydro-pyridine in 600 ml of ethanol are hydrogenated over the course of 4 hours with Raney nickel, activated with 2% of palladium, at 125°–130°C and approx. 100 atmospheres H₂ pressure in an autoclave. After removing the catalyst and the solvent, the product is fractionated through a 40 cm long packed column. Yield: 58.3 g (35.0%); boiling point 126°–29°C/10 mm Hg. The amine forms a dipicrate of melting point 229°C (decomposition) which can be recrystallised from ethanol with addition of a little water. Analysis: $C_6H_{15}N_3 \cdot 2 C_6H_3N_3O_7$ (M = 587.42).

Calculated: C 36.80; H 3.61; N 21.46; Found: C 37.31; H 3.62; N 20.82.

b. 110.7 g of 4-amino-3-cyano-1,2,5,6-tetrahydro-pyridine in a mixture of 300 ml of ethanol and 100 g of ammonia are hydrogenated over the course of 5 hours with 10 g of Raney nickel at 115°–120°C and a pressure of 100 atmospheres in an autoclave. After removing the catalyst and the solvent, the mixture is first distilled in vacuo without a column, whereby 91.4 g of crude amine of boiling point 50°–150°C/7 mm Hg are obtained. The fractional distillation through a rotating strip column yields 82.0 g (70.7%) of pure amine of boiling point 114°–116°C/6.5 mm Hg. Analysis: $C_6H_{15}N_3$ (M= 129.21)

Calculated: C 55.78; H 11.70; N 32.52 Found: C 55.73; H 11.80; N 32.67.

4-Amino-piperidine can be detected as a by-product in the first runnings.

4-Amino-3-aminomethyl-piperidine forms a dipicrate of melting point 229°C (decomposition) and was analysed as such, after recrystallisation from ethanol with the addition of a little water. Analysis: $C_6H_{15}N_3 \cdot 2 C_6H_3N_3O_7$ (M= 587.42)

Calculated: C 36.80; H 3.61; N 21.46; Found: C 37.31; H 3.62; N 20.82.

NMR-spectrum in deuterated dimethylsulphoxide:

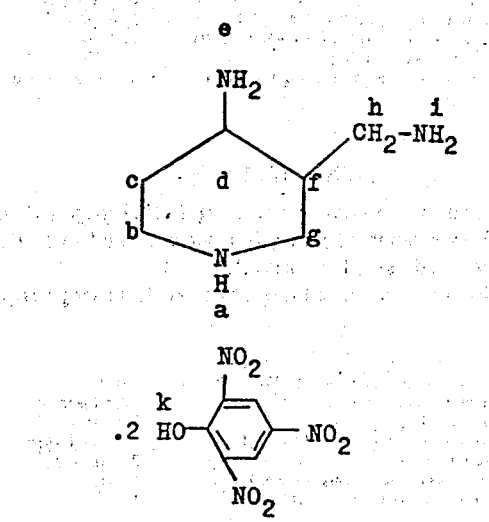

Mass spectrum:

The molecular peak at m/e 129 does not show up. Instead, a fragment, corresponding to splitting off NH₃, appears at m/e 112. The mass spectrum of the free amine also shows the heaviest fragment of mass m/e 112.

| IR-spectrum: Band [cm⁻¹] | Interpretation |
|---|---|
| 3370 m. | NH₂ stretching vibration |
| 3290 m. | NH₂ stretching vibration |
| 3200 shoulder | Harmonic vibration of 1600 cm⁻¹ |
| 1600 m. | NH₂ deformation vibration |

Use Examples

EXAMPLE I 70 parts of epoxide resin A and 9.5 parts of 4-amino-3-aminomethyl-piperidine (corresponding to a ratio of epoxide equivalents: nitrogen-bonded active H atoms = 1.0:1.0) were mixed at room temperature (25°C), degassed in vacuo and poured into aluminium moulds.

The mixture gelled, with an exothermic temperature rise. After cooling, it was post-cured for a further 24 hours at 100°C.

The castings obtained had the following properties:

| | |
|---|---|
| Flexural strength according to VSM 77,103 | = 10.6 kg/mm² |
| Deflection according to VSM 77,103 | = 5.6 mm |
| Impact strength according to VSM 77,105 | = 7.7 cmkg/cm² |

EXAMPLE II 224 parts of epoxide resin B and 25.8 parts of 4-amino-3-aminomethyl-piperidine were mixed at room temperature (25°C), degassed in vacuo, then poured into prewarmed aluminium moulds of size 140 × 140 ×

4 mm and subsequently heated for 4 hours to 80°C and 12 hours to 140°C. The resulting shaped articles had the following properties:

| | |
|---|---|
| Heat distortion point according to DIN 53461 | 92°C |
| Flexural strength according to VSM 77,103 | 11.4 kg/mm² |
| Deflection according to VSM 77,103 | 6.4 mm |
| Impact strength according to VSM 77,105 | 6.8 cmkg/cm² |
| Tensile strength according to VSM 77,101 | 3.4 kg/mm² |
| Elongation at break according to VSM 77,101 | 6.7% |
| Glass transition temperature* | 111°C |

*measured in the Differential Scanning Calorimeter (DSC-1), using a speed of heating of 16°C/min.

EXAMPLE III 155 parts of epoxide resin C and 25.8 parts of 4-amino-3-aminomethyl-piperidine were mixed and further processed as in Example II.

The shaped articles obtained had the following properties:

| | |
|---|---|
| Heat distortion point according to DIN 53461 | 116°C |
| Flexural strength according to VSM 77,103 | 10.5 kg/mm² |
| Deflection according to VSM 77,103 | 3.6 mm |
| Impact strength according to VSM 77,105 | 12.7 cmkg/cm² |
| Tensile strength according to VSM 77,101 | 3.6 kg/mm² |
| Elongation at break according to VSM 77,101 | 6.0% |
| Glass transition temperature (DSC-1) | 127°C |

We claim:
1. In a process for the manufacture of 4-amino-3-aminomethyl-piperidine of the formula

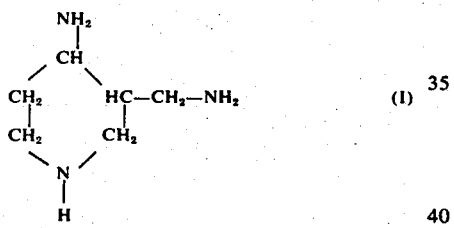

by reduction of 4-amino-3-cyano-1,2,5,6-tetrahydropyridine of the formula

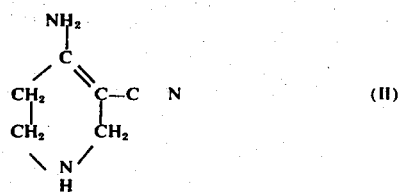

the improvement comprising hydrogenating said 4-amino-3-cyano-1,2,5,6-tetrahydropyridine under pressure and in the presence of ammonia and a hydrogenation catalyst.

2. A process as claimed in claim 1, wherein Raney nickel or Raney cobalt are used as the hydrogenation catalyst.

3. A process as claimed in claim 1, wherein carrier type catalysts containing cobalt are used as the hydrogenation catalyst.

4. A process as claimed in claim 1, wherein hydrogenation catalysts based on platinum and palladium are used as the hydrogenation catalyst.

5. A process as claimed in claim 1, wherein the hydrogenation is carried out in the presence of an organic solvent.

6. A process as claimed in claim 5, wherein a lower aliphatic alcohol is used as the organic solvent.

7. A process as claimed in claim 1, wherein a pressure of 50 to 100 atmospheres is applied.

8. A process as claimed in claim 1, wherein a temperature in the range of 50° to 150°C is applied.

* * * * *